US00PP20141P2

(12) United States Plant Patent
Van Zanten

(10) Patent No.: US PP20,141 P2
(45) Date of Patent: Jun. 30, 2009

(54) ***IRESINE* PLANT NAMED 'AUREO LG'**

(50) Latin Name: *Iresine herbstii*
Varietal Denomination: Aureo LG

(75) Inventor: Leo Van Zanten, Oxnard, CA (US)

(73) Assignee: Grolink Plant Company, Oxnard, CA (US)

( * ) Notice: Subject to any disclaimer, the term of this patent is extended or adjusted under 35 U.S.C. 154(b) by 40 days.

(21) Appl. No.: 11/823,297

(22) Filed: Jun. 27, 2007

(51) Int. Cl.
*A01H 5/00* (2006.01)

(52) U.S. Cl. ..... Plt./263.1
(58) Field of Classification Search ..... Plt./373, Plt./263.1
See application file for complete search history.

*Primary Examiner*—Wendy C. Haas

(57) ABSTRACT

A new and distinct *Iresine* plant cultivar is disclosed, characterized by very distinct leaf color of light green with magenta veins; bright magenta petiole and stems; strong stems; and an upright growth habit.

1 Drawing Sheet

Latin name of the genus and species: *Iresine herbstii.*
Variety denomination: 'AUREO LG'.

BACKGROUND OF THE INVENTION

The new cultivar is the product of an induced mutation. 'AUREO LG' was discovered as a single plant by Leo van Zanten in March 2005 in a cultivated area of Oxnard, Calif. in a greenhouse. Two thousand unrooted cuttings from *Iresine herbstii brilliantissima* were irradiated with gamma rays at a dose of 25 Gy. Treated cuttings were planted for rooting and growing. Subsequent selection as a single plant from the population resulted in the discovery of this new variety.

Asexual reproduction of the new cultivar 'AUREO LG' by terminal cuttings was performed in Oxnard, Calif. and has shown that the unique features of this cultivar are stable and reproduced true to type on successive generations.

SUMMARY OF THE INVENTION

The cultivar 'AUREO LG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AUREO LG.' These characteristics in combination distinguish 'AUREO LG' as a new and distinct *Iresine* cultivar:

1. Very distinct leaf color of light green with magenta veins;
2. Bright magenta petiole and stems;
3. Strong stems; and
4. Upright growth habit.

Plants of the new cultivar 'AUREO LG' are similar to plants of the parent variety, *Iresine herbstii brilliantissima* (not patented) in most horticultural characteristics, however, plants of the new cultivar 'AUREO LG' have an upright growth habit compared to the compact growth habit of the parent. Additionally, the new variety 'AUREO LG' has a longer longevity of several weeks compared to the parent.

Finally, the new variety 'AUREO LG' has lime green foliage compared to the dark purple colored foliage of the parent.

In comparison to variety 'AUREO M' (U.S. Plant patent application No. 11/823,299) 'AUREO LG' has lime green foliage with magenta veins compared to the dark purple foliage with magenta veins of 'AUREO M'.

In comparison to the commercially available variety 'Aureo-reticulata' (unpatented) the new cultivar 'AUREO LG' has ovate lanceolate shaped leaves compared to the rounded leaves of the unpatented variety 'Aureo-reticulata.' Also, the stems and the petioles are a bright red-purple compared to the dark red stems and petioles of the unpatented variety. Finally, the new cultivar 'AUREO LG' has a taller and wider plant habit.

BRIEF DESCRIPTION OF THE PHOTOGRAPH

The accompanying photograph in the drawing illustrates in full color a typical plant of 'AUREO LG' grown in a outdoor garden. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'AUREO LG' plants grown in Oxnard, Calif. during the months of January through April. The growing temperature ranged from 12° C. to 15° C. at night to 12° C. to 20° C. during the day. Measurements and numerical values represent averages of typical plant types.

Botanical classification: *Iresine herbstii* cultivar 'AUREO LG.'
Commercial classification: Bloodleaf.

PROPAGATION

Time to initiate roots: 12 days at 22–25° C.
Time to develop roots: 17 days at 22–25° C.
Root Description: Fine, fibrous, white in color.

PLANT

Plant type: Annual.
Growth habit: Upright.
Height: Approximately 29 cm.
Plant spread: Approximately 30 cm.
Growth rate: Moderate.
Branching characteristics: Opposite, decussate.
Number of lateral branches per plant: 5.
Length of lateral branches: Approximately 18 cm.
Diameter of lateral Branches: Approximately 0.5 cm.
Number of leaves per lateral branch: Approximately 30.
Stem and stem base strength: Strong.
Stem texture: Lightly pubescent.
Stem habit: Ascending.
Age of plant described: Approximately 98 days.

FOLIAGE

Leaf:
*Arrangement.*—Opposite.
*Average length.*—Approximately 5.9 cm.
*Average width.*—Approximately 4.4 cm.
*Shape of blade.*—Ovate to ovate lanceolate.
*Apex.*—Acuminate.
*Base.*—Oblique.
*Attachment.*—Petiolate.
*Margin.*—Cleft.
*Texture of top surface.*—Lightly pubescent.
*Texture of bottom surface.*—Lightly pubescent.
*Leaf internode length.*—Approximately 7 cm.
Color:
Developing foliage on the upper surface:
*Towards the margins.*—Near Green 137A.
*Center.*—Near Yellow-Green 154C.
*Towards the base.*—Near Yellow-Green 154D.
*Venation.*—Near Red-Purple 58A.
Developing foliage on the lower surface:
*Towards the margins.*—Near Green 138B.
*Center.*—Near Green 13C.
*Towards the base.*—Near Yellow-Green 154D.
*Venation.*—Near Red-Purple 58A.
Fully expanded foliage on the upper surface:
*Towards the margins.*—Near Green-Yellow 1D.
*Towards the center.*—Near Green 137B.
*Center.*—Near Green 137C and Green-Yellow 1D.
*Towards the base.*—Near Green-Yellow 1D.
*Venation.*—Near Red-Purple 63A.
Fully expanded foliage on the lower surface:
*Towards the margins.*—Near Green-Yellow 1D.
*Towards the center.*—Near Green 138B.
*Center.*—Near Green 138C and Green-Yellow 1D.
*Towards the base.*—Near Green-Yellow 1D.
*Venation.*—Near Red-Purple 63A.
Petiole:
*Average length.*—Approximately 2.7 cm.
*Color.*—Near Red-Purple 63A.
*Diameter.*—Approximately 0.3 cm.

FLOWER

'AUREO LG' does not produce flowers.

OTHER CHARACTERISTICS

Disease resistance: Neither resistance nor susceptibility to diseases or pests has been observed in this variety.
Drought tolerance cold tolerance: Plants are hardy in the approximate range of 3° C. to 6° C., depending upon duration of cold and amount of moisture in the soil. With adequate water plants are hardy to a high temperature of 45° C.

What is claimed is:

1. A new and distinct cultivar of *Iresine* plant named 'AUREO LG' as herein illustrated and described.

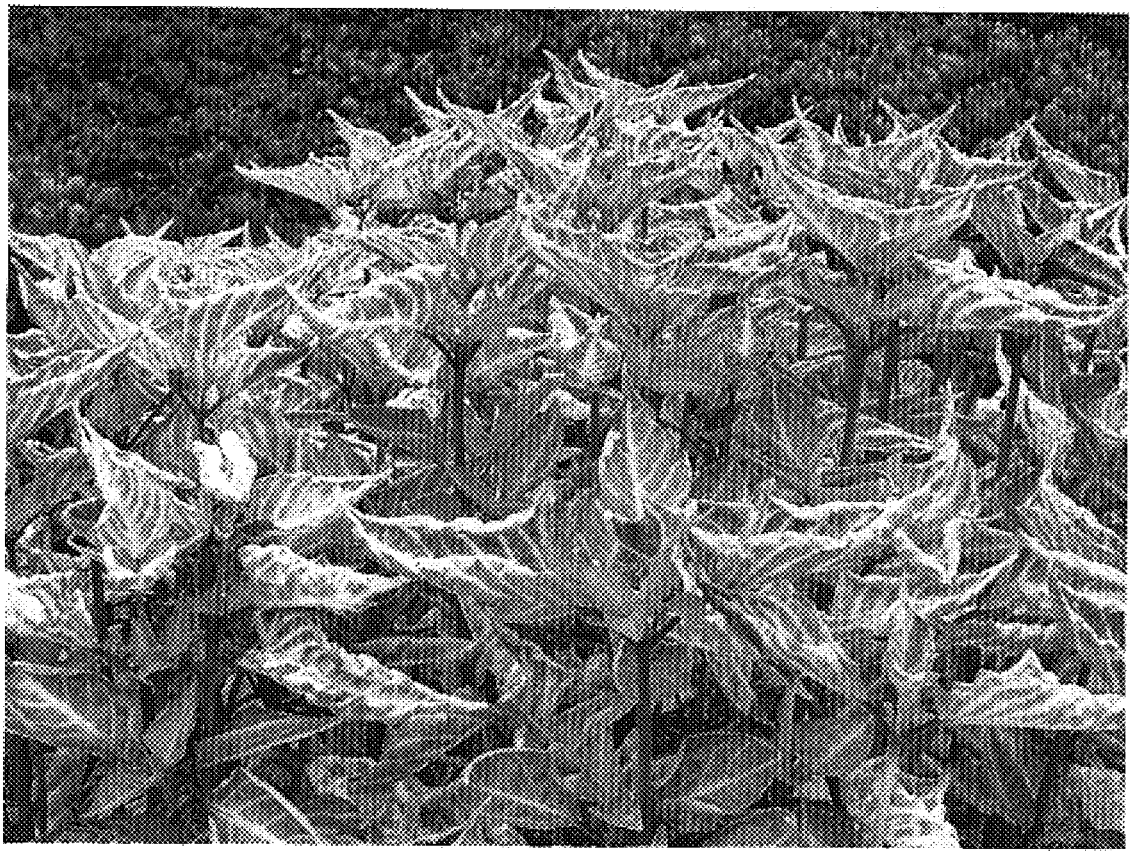

* * * * *